United States Patent
Van Krieken et al.

(10) Patent No.: US 10,118,908 B2
(45) Date of Patent: Nov. 6, 2018

(54) METHOD FOR MANUFACTURING FURAN-2,5-DICARBOXYLIC ACID (FDCA) FROM A SOLID SALT

(71) Applicant: PURAC BIOCHEM BV, Gorinchem (NL)

(72) Inventors: Jan Van Krieken, Gorinchem (NL); Andre Banier De Haan, Gorinchem (NL)

(73) Assignee: PURAC BIOCHEM B.V., Gorinchem (NL)

( * ) Notice: Subject to any disclaimer, the term of this patent is extended or adjusted under 35 U.S.C. 154(b) by 0 days.

(21) Appl. No.: 15/558,247

(22) PCT Filed: Mar. 17, 2016

(86) PCT No.: PCT/EP2016/055818
§ 371 (c)(1),
(2) Date: Sep. 14, 2017

(87) PCT Pub. No.: WO2016/146752
PCT Pub. Date: Sep. 22, 2016

(65) Prior Publication Data
US 2018/0099942 A1  Apr. 12, 2018

(30) Foreign Application Priority Data
Mar. 17, 2015 (EP) .................................. 15159401

(51) Int. Cl.
C07D 307/68  (2006.01)
(52) U.S. Cl.
CPC .................... *C07D 307/68* (2013.01)
(58) Field of Classification Search
CPC .................................................. C07D 307/68
See application file for complete search history.

(56) References Cited

U.S. PATENT DOCUMENTS

2014/0357877 A1* 12/2014 De Haan ................. C01B 7/035
549/485

FOREIGN PATENT DOCUMENTS

| KR | 10-2014-0057607 A | 5/2014 |
| WO | 2011/026913 A1 | 3/2011 |
| WO | 2013/025106 A1 | 2/2013 |

OTHER PUBLICATIONS

Jun. 16, 2016 International Search Report issued in Patent Application No. PCT/EP2016/055818.
Jun. 16, 2016 Written Opinion issued in Patent Application No. PCT/EP2016/055818.
Apr. 15, 2018 Office Action issued in Korean Application No. 10-2017-7029395.

* cited by examiner

*Primary Examiner* — Timothy R Rozof
(74) *Attorney, Agent, or Firm* — Oliff PLC

(57) ABSTRACT

A method for manufacturing furan-2,5-dicarboxylic acid (FDCA) by converting a furan-2,5-dicarboxylate salt (MFDC) into furan-2,5-dicarboxylic acid (FDCA), includes the steps of combining solid MFDC with an inorganic acid (HY), to form a reaction mixture having solid FDCA in a concentration of 1-15 wt. % in a solution of a salt resulting from the cation of the furan-2,5-dicarboxylate salt and the anion of the inorganic acid (MY solution), removing solid FDCA from the reaction mixture in a solid/liquid separation step, and providing at least 40 vol. % of the MY solution resulting from the solid/liquid separation step to the step of combining MFDC with HY. The step of providing part of the MY salt solution resulting from the solid/liquid separation step to the step of combining MFDC with HY makes it possible to obtain a stable and economic process which results in an FDCA product with good quality, and obtained in high yield.

12 Claims, 3 Drawing Sheets

US 10,118,908 B2

METHOD FOR MANUFACTURING FURAN-2,5-DICARBOXYLIC ACID (FDCA) FROM A SOLID SALT

The present invention pertains to a method for manufacturing furan-2,5-dicarboxylic acid (FDCA) from a solid salt.

FDCA is an attractive material for numerous applications, among others as starting material for polymer production, where FDCA-based copolymers are an alternative to, among others, polyethylene terephthalic acid polymers (PET). FDCA esters may also find use as plasticizers or cross-linkers. The dimethylester of FDCA may be of particular interest for polymerisation. Esters of higher alcohols, e.g., dibutyl FDCA, diethylhexyl FDCA, and dioctyl FDCA may be of particular interest for use as plasticizers and in polymers and coatings.

FDCA can be manufactured through various methods. One method, which is particularly attractive is a fermentation-based process starting from renewable resources. In this manner, FDCA can be obtained in an environmentally friendly manner.

As is known in the art, the manufacture of FDCA through fermentation generally takes the form of a fermentative biooxidation of 5-(hydroxymethyl) furfural (HMF). This is, e.g., described in WO2011/026913. The liquid wherein the process is carried out is called the fermentation broth or the fermentation medium. The formation of FDCA in the process will result in a decrease of the pH of the fermentation broth. Since such a decrease in pH can damage the microorganism's metabolic process, a neutralizing agent, i.e. a base, is often added to the fermentation medium in order to neutralize the pH or to maintain an optimum pH value for the micro-organisms.

In consequence, the FDCA produced in the fermentation medium is typically present in the form of a salt, which may be dissolved in the fermentation medium, present in the form of a solid salt, or both dissolved in the fermentation medium and present in the form of a solid salt.

To convert the salt of FDCA to the acid, it has been envisaged to react the salt of FDCA with an inorganic acid, to yield FDCA and a salt built up from the cation of the salt of FDCA and the anion of the inorganic acid. For example, WO2013/025106 describes acidification of, among others, magnesium FDC with hydrochloric acid.

However, while this reaction is simple and elegant in theory, it has been found that when carrying it out in practice, various operational problems occur, which make it difficult to operate the reaction in a stable an economically attractive manner, while obtaining FDCA with high product quality. In WO2013/025106 the acidification reaction is carried out at high dilution, in view of the low solubility of MgFDC. In Example 1 an MgFDC solution with a concentration of 1.7 wt. % is used. As will be clear to the skilled person, highly diluted solutions are disadvantageous for at least two reasons. In the first place, they require relatively large investments in apparatus. In the second place, the presence of large amounts of water in the process results in the loss of FDCA product by dissolution in the reaction mixture.

There is therefore need in the art for a method for converting FDCA salts into FDCA via acidification in a method which does not necessitate the use of highly diluted solutions, which allows stable operation in an economically attractive manner, while obtaining FDCA with high product quality and high yield. The present invention provides such a method.

The present invention pertains to a method for manufacturing furan-2,5-dicarboxylic acid (FDCA) by converting a furan-2,5-dicarboxylate salt (MFDC) into furan-2,5-dicarboxylic acid (FDCA), comprising the steps of
  combining solid MFDC with an inorganic acid (HY), to form a reaction mixture comprising solid FDCA in a concentration of 1-15 wt. % in a solution of a salt resulting from the cation of the furan-2,5-dicarboxylate salt and the anion of the inorganic acid (MY solution),
  removing solid FDCA from the reaction mixture in a solid/liquid separation step, and
  providing at least 40 vol. % of the MY solution resulting from the solid/liquid separation step to the step of combining MFDC with HY.

It is noted that some salts of FDCA, in particular, MgFDC and CaFDC, have a limited solubility in water. FDCA also has a low solubility in water. In consequence, the above process encompasses conversion from a solid compound into a solid compound. These types of reactions are generally avoided in chemistry because they are difficult to carry out at high yield while obtaining high product purity. In the present invention, however, it has been found that it is in fact possible to carry out this process.

A further feature of the present process is the following. As indicated above, FDCA has a low solubility in water. In theory, this would be expected to make it easy to separate the FDCA from an aqueous mixture containing the other reactant components. However, due to the specific shape of the FDCA crystals, it has been found that concentrated suspensions of FDCA are difficult to process. On the other hand, dilution of the FDCA suspension leads to a loss in yield because more FDCA will dissolve. Therefore, the properties of solid FDCA require specific measures.

The present process, with the specific features of starting out from a solid FDCA salt in combination with a specific recycle makes it possible to obtain FDCA of good quality with low product loss, while at the same time having a process which is stable and can be carried out in practice.

The invention will be discussed in more detail below.

The present invention will be elucidated with reference to the following Figures, without being limited thereto or thereby.

Figure 1:
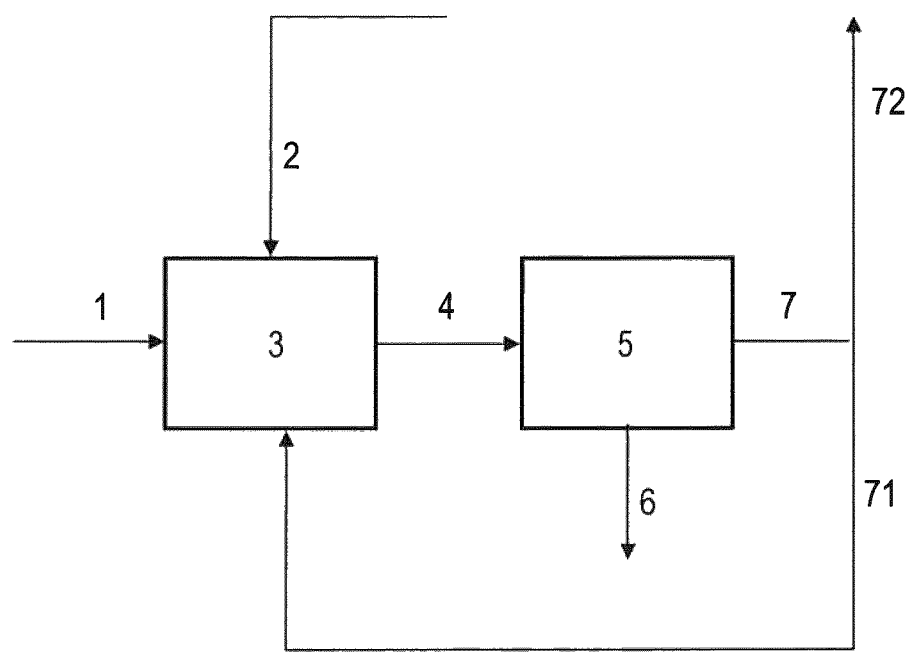
FIG. 1 illustrates a first embodiment of the present invention.

In FIG. 1, a furan-2,5-dicarboxylate salt (MFDC) is provided through line (1) to a reaction vessel (3). The MFDC is present in solid form. Inorganic acid (HY) is provided to reaction vessel (3) through line (2). The reaction vessel is also provided with a salt solution (MY solution) through line (71). In the reaction vessel, MFDC reacts with HY to form FDCA and MY, and the reaction mixture comprising FDCA and HY is transferred through line (4) to a solid/liquid separation step (5). Although not depicted in FIG. 1, it is of course also possible to carry out the solid liquid separation step in the reaction vessel. In solid liquid separation step (5), the solid FDCA is separated from the MY salt solution, and withdrawn through line (6). The salt solution is withdrawn through line (7). At least 40 vol. % of the salt solution is provided to reaction vessel (3) through line (71). Another part of the salt solution is withdrawn through line (72).

The method according to the invention starts out from a salt of furan-2,5-dicarboxylic acid (MFDC). The salt is present in solid form, e.g., as dry material, in the form of a filter cake, or in the form of a suspension.

The furan-2,5-dicarboxylate salt is preferably selected from magnesium furan-2,5-dicarboxylate (MgFDC), calcium furan-2,5-dicarboxylate (CaFDC), sodium furan-2,5-dicarboxylate (NaFDC), potassium furan-2,5-dicarboxylate (KFDC), or ammonium furan-2,5-dicarboxylate (NH4FDC). These salts have been found to be attractive as starting materials because they can be obtained relatively easy, e.g., from fermentation processes. On the other hand, it has been found that when they are used in the process according to the invention, FDCA is obtained in high yield and with high product quality and process efficiency.

In one embodiment, the MFDC is selected from MgFDC and CaFDC, with MgFDC being particularly preferred. In view of their low solubility in water, these salts are particularly suitable for processing in the method according to the invention, as processing them in dissolved form will lead to the use of highly diluted solutions. Further, MgFDC and CaFDC, in particular MgFDC, have been found to be attractive because of their availability and the high quality of the product obtained. For MgFDC there is an additional processing advantage when it is processed in the presence of HCl. This will be discussed in more detail below.

The solid MFDC can, e.g., be in the form of a dry material, in the form of a filter cake, or in the form of a suspension. Where a filter cake is used, it generally has a solids content of 90-50 wt. % (the balance being an aqueous solution of MFDC), with higher solids content being preferred. Where an (aqueous) suspension is used, it generally has a solids content of 10-50 wt. %, in particular 20-40 wt. %.

In another embodiment of the present invention, the MFDC is selected from NaFDC, KFDC, and NH4FDC. For NaFDC, KFDC, and NH4FDC it is also possible to provide the salts in solid form, e.g., in the form of dry material, filter cake, or a suspension. For these salts it is preferred to provide the salts in the form of dry material or a filter cake.

The MFDC is combined with an inorganic acid (HY), to form a reaction mixture comprising solid FDCA in a solution of a salt resulting from the cation of the MFDC and the anion of the inorganic acid (MY solution).

As will be evident to the skilled person, in the process according to the invention, the combination of acid and salt has to be selected in such a manner that the cation M of the MFDC and the anion Y of the inorganic acid HY results in the formation of a salt with a solubility in water which is so high that no salt precipitates under process conditions. For example, the combination of CaFDC and sulphuric acid is not suitable, because it results in the formation of calcium sulphate, which will precipitate. A solubility of the MY salt of at least 10 wt. % will generally be sufficient.

The inorganic acid added in the process according to the invention serves to convert the FDCA salt to the acid. Depending on the nature of the inorganic acid and on the other components present in the system, the inorganic acid can be provided in the form of an aqueous solution, or, e.g., in the case of hydrochloric acid, in gaseous form. The inorganic acid is generally a strong inorganic acid, i.e., an acid with pKa of below zero. Examples of suitable acids are sulphuric acid, hydrochloric acid, nitric acid, phosphoric acid, hydrobromic acid, and derivatives thereof such as $NH_4HSO_4$. The use of sulphuric acid, hydrochloric acid, and nitric acid, may be preferred, with the use of hydrochloric acid being particularly preferred.

The acid concentration of an aqueous solution is generally not critical to the present invention. Concentrated solutions, e.g., with an acid concentration of at least 5%, in particular at least 10%, more in particular at least 15 wt. %, are generally preferred for reasons of process economy. The maximum concentration will be determined to the solubility or miscibility of the acid in question. A general value of at most 35 wt. % may be mentioned. The use of concentrated HY solutions is preferred because it limits the amount of water in the system.

The amount of acid to be added will generally be at least sufficient to neutralise the FDCA salt. This can easily be calculated from the amount of FDCA salt present, and be determined by monitoring the pH of the reaction medium. It is preferred for the pH of the reaction medium to be at most 2. It may be preferred for the pH of the reaction medium to be in the range of 1 to 2, to combine a high FDCA yield with the avoidance of a high excess of acid, as this may be detrimental to processing apparatus, or may result in unnecessary recycle of materials.

Examples of combinations of FDCA salt and inorganic acid which yield a soluble inorganic salt include the following:

sodium FDCA and any of sulphuric acid, hydrochloric acid, hydrobromic acid, phosphoric acid, and nitric acid;

potassium FDCA and any of sulphuric acid, hydrochloric acid, hydrobromic acid, phosphoric acid, and nitric acid;

ammonium FDCA and any of sulphuric acid, hydrochloric acid, hydrobromic acid, phosphoric acid, and nitric acid;

calcium FDCA and any of hydrochloric acid, hydrobromic acid, and nitric acid;

magnesium FDCA and any of sulphuric acid hydrochloric acid, hydrobromic acid, and nitric acid.

In one embodiment of the present invention, the inorganic acid (HY) is selected from hydrochloric acid, nitric acid, and sulphuric acid, with the proviso that where the MFDC is CaFDC, the inorganic acid (HY) is selected from hydrochloric acid and nitric acid.

In a preferred embodiment of the present invention, the inorganic acid (HY) is hydrochloric acid HCl and the MFDC is MgFDC, and the method encompasses in a combination step combining solid MgFDC with hydrochloric acid in a magnesium chloride solution to form a reaction mixture comprising solid FDCA in a concentration of 1-15 wt. % in a magnesium chloride solution, removing solid FDCA from the reaction medium in a solid/liquid separation step, and providing at least 40 vol. % of the magnesium chloride solution resulting from the solid/liquid separation step to the step of combining solid magnesium chloride with hydrochloric acid.

In the method according to the invention, the amount of MFDC and its water content, the amount of acid and its concentration, and the amount of MY solution which are combined will be selected in such a manner that the FDCA concentration in the reaction mixture is within the range of 1-15 wt. %, in particular 1-10 wt. %. If the amount of FDCA in the reaction mixture is below 1 wt. %, the volume stream to be processed is unnecessarily large. On the other hand, if the amount of FDCA formed is above 15 wt. % it has been found that the processability of the reaction mixture and the subsequent solid liquid separation are detrimentally affected. In some cases it may be preferred for the amount and concentration of the various components to be selected such that the amount of FDCA formed is within the range of 2 to 8 wt. %, in particular 3-7 wt. %, calculated on the total weight of the reaction mixture. The amount of FDCA here is the amount of solid FDCA. As FDCA has a low solubility in this system, the total amount of FDCA and the amount of solid FDCA are about equal.

The solid FDCA is removed from the reaction mixture in a solid/liquid separation step. The solid/liquid separation step can be carried out by methods known in the art, e.g., methods encompassing one or more of filtration, centrifugation, sedimentation, or using hydrocyclones. The use of filtration is often preferred.

The FDCA separated in the solid liquid separation step can be processed as desired. If so desired it can be subjected to a washing step.

After removal of the solid FDCA, a salt solution remains, of which the cation corresponds with the cation of the original FDCA salt (M), and the anion corresponds to the anion of the inorganic acid (Y). It is a feature of the present invention that of the salt solution remaining after the solid/liquid separation step, at least 40 vol. % is recycled to the step of combining the salt of FDCA with the inorganic acid.

The amount of MY solution which is recycled is selected such that the amount of solid FDCA formed is within the ranges stipulated above. The amount of MY solution which is recycled thus also depends on the concentration of the acid provided, and on the form in which the MFDC is provided. It is preferred for a substantial part of the MY solution to be provided to the step of combining the salt of FDCA with the inorganic acid.

It has been found that the presence of a relatively large amount of MY solution in the step of combining MFDC with HY results in a higher FDCA yield. Not wishing to be bound by theory, it is believed that this is caused by the fact that the solubility of FDCA in an MY solution is, at least for some salts, lower that the solubility of FDCA in water. Therewith, the presence of the salt solution is believed to result in increased precipitation of solid FDCA as compared to a system wherein a corresponding amount of water would be present. It may be preferred if at least 50 vol. % of the MY solution resulting from the solid/liquid separation step is provided to the step of combining MFDC with HY, in particular at least 60 vol. %, in some embodiments at least 70 vol. % and/or at most 95 vol. %.

The concentration of the MY solution, e.g. the magnesium chloride solution, withdrawn from the solid liquid separation step may vary within wide ranges. As a minimum, a value of at least 5 wt. % may be mentioned, in particular at least 10 wt. %. The upper limit will be determined by the solubility of the MY salt. As a general maximum, a value of 30 wt. % may be mentioned. A range of 10-20 wt. % may be preferred.

The MFDC can, e.g., be obtained from a fermentation process, wherein an aqueous feed comprising an FDCA salt is formed. Such a step typically comprises the substeps of fermenting a carbon source by means of a micro-organism, and forming a fermentation medium comprising FDCA, and, generally during fermentation (partially) neutralizing the fermentation medium in order to establish a desirable pH by adding a neutralizing agent, i.e. a base. Suitable bases include oxides, hydroxides, and carbonates of sodium, potassium, ammonium, calcium and magnesium.

As indicated above, the manufacture of FDCA through fermentation generally takes the form of a fermentative biooxidation of 5-(hydroxymethyl) furfural (HMF). These processes are known in the art and it is within the scope of the skilled person to select a fermentation process leading to the formation of FDCA.

The fermentation medium is generally subjected to a biomass removal step. Biomass can, e.g., be removed by (ultra)filtration, centrifugation or decantation of the biomass. Biomass removal has been found to result in an end product with improved properties.

Where the FDCA salt is soluble in water, after biomass removal, a solution comprising dissolved FDCA salt is thus obtained, which can be used as starting material in the process according to the invention, optionally after further purification and/or water removal steps.

Where the fermentation broth comprises FDCA salt in the solid state, the FDCA salt can be separated from the fermentation broth via solid-liquid separation methods such as filtration, or one of the other methods discussed above. The solid FDCA salt thus obtained can be used as starting material in the process according to the invention, optionally after further purification steps.

As has been indicated above, in a preferred embodiment of the present invention the MFDC starting material is magnesium FDC while the inorganic acid is hydrochloric acid. In this case, the MY solution will be a magnesium chloride solution. Within this embodiment it may be preferred for a part of the magnesium chloride solution obtained in the solid liquid separation step to be provided to a thermal decomposition step. In a thermal decomposition step, magnesium chloride is converted into magnesium oxide and hydrochloric acid. The process of thermal decomposition is also known under the terms thermal hydrolysis and thermohydrolysis. The magnesium chloride solution can be provided directly to the thermohydrolysis step, or after intermediate steps such as a concentration step or a drying step.

Thermal decomposition is generally conducted at a temperature of a least 300° C. Preferably, thermal decomposition is conducted at a temperature of at least 350° C. Due to energy costs, the temperature is preferably below 1000° C., more preferably below 800° C. For example, the temperature at which thermal decomposition is conducted may be 350-800 or 400-600° C.

Where a magnesium chloride solution is provided to a thermal decomposition step, the magnesium chloride solution preferably has a magnesium chloride concentration of 15-40 wt. %, more preferably 25-35 wt. %. Too high amounts of magnesium chloride present in the solution may result in precipitation of magnesium chloride upon entering the thermohydrolysis unit. Water may be added to or removed from the magnesium chloride solution recovered in this embodiment of the present invention in order to obtain a desirable magnesium chloride concentration.

Suitable apparatuses for conducting thermal decomposition are known in the art. For example, a spray roaster or a fluid bed roaster can be used. Such apparatuses can for example be obtained at SMS Siemag, Andritz. Tenova, CMI, and Chemline. The magnesium oxide obtained in thermal decomposition will be in solid form. In one embodiment of the present invention, the magnesium oxide is provided, directly or after conversion into a hydroxide or carbonate, as neutralising agent to a fermentation step, preferably a fermentation step wherein a carbon source is fermented by means of a micro-organism in a fermentation broth and FDCA is formed.

In one embodiment of the invention, the hydrochloric acid resulting from the thermal decomposition step is provided to a step of combining magnesium FDC with an inorganic acid (HY), to form a reaction mixture comprising solid FDCA in a solution, in accordance with the present invention. It is particularly preferred to carry out both the magnesium oxide recycle step and the hydrochloric acid recycle step as described above.

Figure 2:
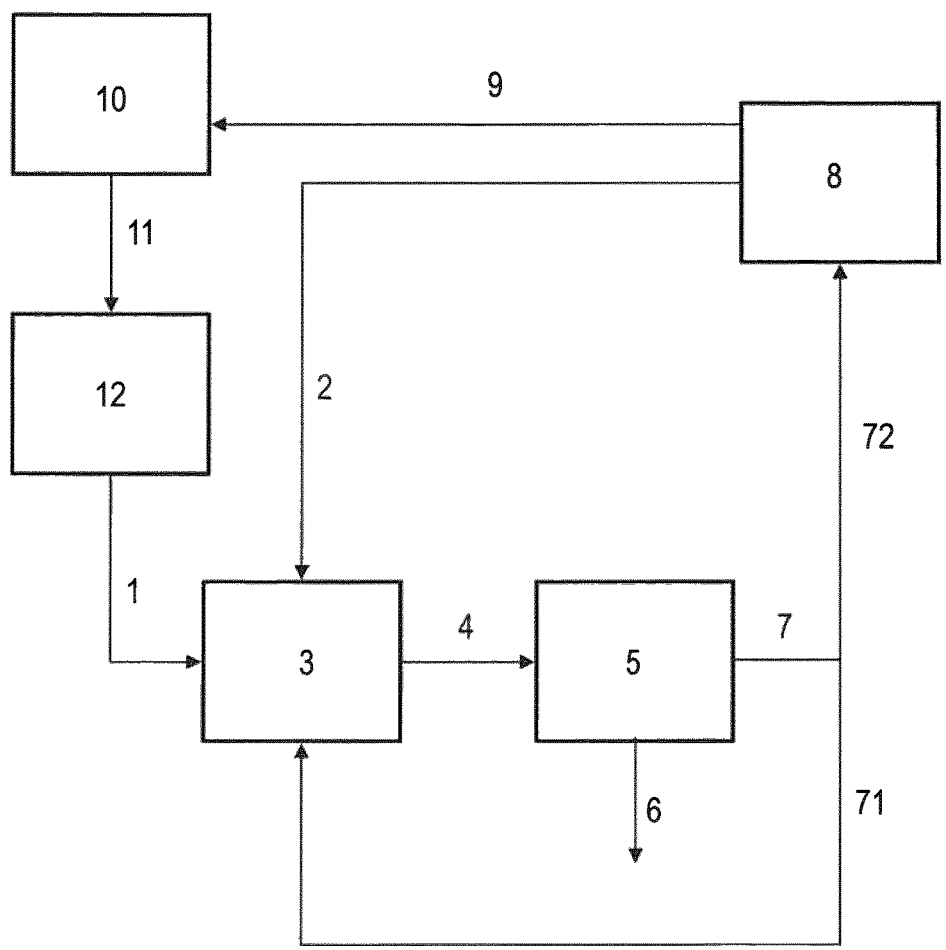
FIG. 2 illustrates an embodiment specifically applicable to acidulation of magnesium furan-2,5-dicarboxylate with HCl, which encompasses various recycle streams.

FIG. 2 illustrates an embodiment specifically applicable to acidulation of MgFDC with HCl, which encompasses various recycle streams.

In FIG. 2, MgFDC is provided through line (1) to a reaction vessel (3). Hydrochloric acid is provided to reaction vessel (3) through line (2). The reaction vessel is also provided with a magnesium chloride through line (71). In the reaction vessel, MgFDC reacts with HCl to form FDCA and (dissolved) magnesium chloride, and the reaction mixture comprising FDCA and magnesium chloride in solution is transferred through line (4) to a solid/liquid separation step (5). Although not depicted, it is of course also possible to carry out the solid liquid separation step in the reaction vessel. In solid/liquid separation step (5), the solid FDCA is separated from the magnesium chloride salt solution, and withdrawn through line (6). The magnesium chloride solution is withdrawn through line (7). Part of the magnesium chloride solution is provided to reaction vessel (3) through line (71). Another part of the magnesium solution is withdrawn through line (72) and provided to thermal decomposition unit (8). In the thermal decomposition unit, the magnesium chloride is converted into magnesium oxide and hydrochloric acid. The hydrochloric acid is withdrawn from the thermal decomposition unit (8) through line (2) and provided to the reaction vessel (3). The hydrochloric acid is formed in the thermal decomposition unit is gaseous form. It can be provided to reaction vessel (3) in gaseous form, but it can also first be dissolved in water to form a hydrochloric acid solution in a dissolution unit (not shown). The magnesium oxide is withdrawn from the thermal decomposition unit (8) through line (9), and provided to a fermentation unit (10) as neutralizing agent, either directly or after conversion into magnesium hydroxide or carbonate. In fermentation unit (10), a carbon source is fermented by means of a micro-organism in a fermentation broth to form magnesium FDC. Fermentation broth is removed through line (11), optionally subjected to a biomass removal step (not shown), and provided to a solid-liquid separation step (12), where solid magnesium FDC is separated. The solid magnesium FDC is withdrawn and provided through line (1) to reaction vessel (3). Optionally, the solid magnesium FDC may be subjected to intermediate processing, e.g., a washing step (not shown).

It will be evident to the skilled person that the various aspects of the present invention which are described above in different paragraphs may be combined.

The invention will be elucidated by the following examples, without being limited thereto or thereby.

EXAMPLE 1: SOLUBILITY OF FDCA IN WATER AS A FUNCTION OF MAGNESIUM CHLORIDE CONCENTRATION

Magnesium chloride solutions in water were prepared by dissolving magnesium chloride hexahydrate in water. To each solution (30 g) solid FDCA was added and the mixture was stirred for 24 h at 21.8° C. After stirring a sample was taken and filtered by means of a 0.45 micron filter. The clear filtrate was analysed on FDCA content by means of HPLC. The experiment was repeated at 48.8° C. The results are presented in FIG. 3.

Figure 3:
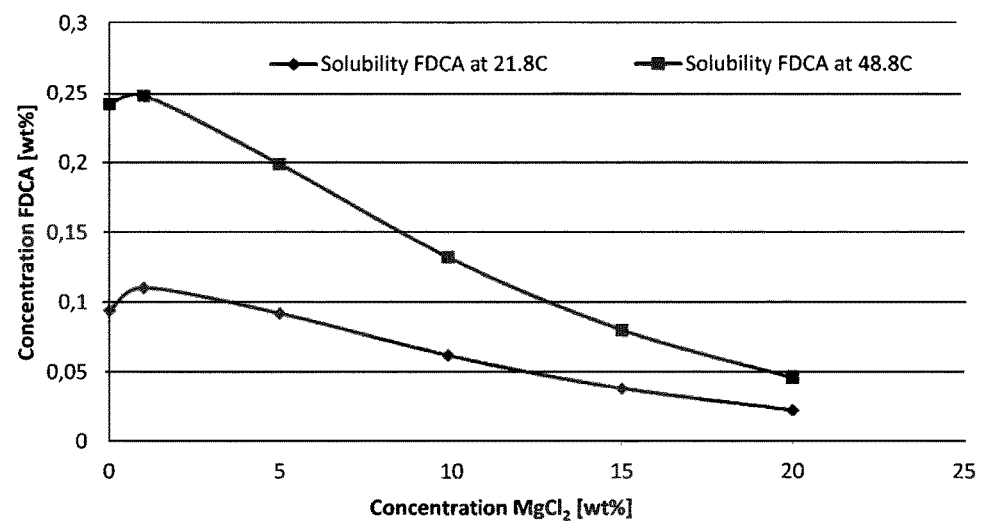
FIG. 3 shows the solubility of FDCA in water as a function of the magnesium chloride concentration at different temperatures.

It can be seen from FIG. 3 that the solubility of FDCA depends strongly on temperature and on the concentration of magnesium chloride. This shows that the presence of MY solution in the step of combining MFDC with HY results in an increased yield of FDCA.

EXAMPLE 2: COMPARATIVE: ACIDULATION OF A SOLUTION OF MGFDC WITHOUT RECYCLE OF MY SOLUTION

1 L of a 4 wt. % (as anhydrate) solution of MgFDC was acidulated with 20 wt. % of hydrochloric acid and heated to 50° C. in a stirred reactor.

The HCl was added over a period of about 1 hour and the final pH was 1.5. The final mixture had an FDCA content of 3.2 wt. % and an MgCl2 content of 2.0 wt. %. The solid FDCA was filtered off and washed with water. The concentration of 4 wt. % was chosen as it is the saturation concentration at 20° C.

The example shows that FDCA can be obtained by acidulation of a solution of MgFDC, but that a very diluted magnesium chloride solution is obtained. Also a significant part of the FDCA will remain in solution. This example thus shows the disadvantages of carrying out the acidulation reaction in the absence of a MY solution.

EXAMPLE 3: COMPARATIVE: ACIDULATION WITHOUT DILUTION

A jacked glass vessel of 150 ml was controlled at 20° C. by means of a thermostatic bath, and charged with 50.03 g of MgFDC.6H2O (175 mmol). Hydrochloric acid 20 wt. % (62.8 g, 344 mmol) was added in three portions, while mixing mechanically/manually. The result was a white, non-pumpable paste with small lumps and a pH of 0.

The example shows that direct acidulation of MgFDC.6H2O with 20 wt. % HCl results in a non-processable paste. The paste has an FDCA concentration of 23-24 wt. %.

EXAMPLE 4: ACIDULATION OF MGFDC WITH HCL WITH ADDITION OF MY SOLUTION

MgFDC.6H2O (42.75 g, 0.15 mol) was suspended in 128.25 g of a 14 wt. % magnesium chloride (MgCl2) solution in water.

A reactor was charged with 174.3 g of 14 wt. % MgCl2 solution in water and heated to 100° C. The suspension of MgFDC.6H2O in 14 wt. % MgCl2 was added to the reactor in a period of 45 minutes. During the addition the pH was kept constant at 1.5 by adding simultaneously a 20 wt. % solution of hydrochloric acid in water.

The final mixture had an FDCA content of 5.7 wt. % and an MgCl2 content of 16 wt. %. The slurry was stirred without problems. The solid FDCA was filtered off and washed with water. In this experiment the total magnesium chloride solution recycle was 69 vol. %.

This example shows that when using a (recycled) magnesium chloride solution, no additional water has to be added to suspend the MgFDC.6H2O crystals. Furthermore a good processable suspension is obtained after acidulation, which assures easy solid-liquid separation of the FDCA. Further, the amount of dissolved FDCA will be very low as the concentration of magnesium chloride in the liquid is relatively high.

The invention claimed is:

1. Method for manufacturing furan-2,5-dicarboxylic acid (FDCA) by converting a furan-2,5-dicarboxylate salt (MFDC) into furan-2,5-dicarboxylic acid (FDCA), comprising the steps of
    combining solid MFDC with an inorganic acid (HY), to form a reaction mixture comprising solid FDCA in a concentration of 1-15 wt. % in a solution of a salt resulting from the cation of the furan-2,5-dicarboxylate salt and the anion of the inorganic acid (MY solution),
    removing solid FDCA from the reaction mixture in a solid/liquid separation step, and
    providing at least 40 vol. % of the MY solution resulting from the solid/liquid separation step to the step of combining MFDC with HY.

2. Method according to claim 1, wherein the salt of furan-2,5-dicarboxylate is selected from magnesium furan-2,5-dicarboxylate (MgFDC), calcium furan-2,5-dicarboxylate (CaFDC), sodium furan-2,5-dicarboxylate (NaFDC), potassium furan-2,5-dicarboxylate (KFDC), and ammonium furan-2,5-dicarboxylate (NH4FDC).

3. Method according to claim 1, wherein the inorganic acid (HY) is selected from hydrochloric acid (HCl), nitric acid (HNO3), and sulphuric acid (H2SO4), with the proviso that where the salt of furan-2,5-dicarboxylate is CaFDC, the inorganic acid (HY) is selected from hydrochloric acid (HCl) and nitric acid (HNO3).

4. Method according to claim 1, wherein the inorganic acid (HY) is hydrochloric acid (HCl) and the salt of furan-2,5-dicarboxylate is MgFDC, wherein the method encompasses in a combination step combining solid MgFDC with hydrochloric acid in a magnesium chloride solution to form a reaction mixture comprising solid FDCA in a concentration of 1-15 wt. % in a magnesium chloride solution,
    removing solid FDCA from the reaction medium in a solid/liquid separation step, and
    providing at least 40 vol. % of the magnesium chloride solution resulting from the solid/liquid separation step to the step of combining solid magnesium chloride with hydrochloric acid.

5. Method according to claim 1, wherein the amount of MFDC and its water content, the amount of acid and its concentration, and the amount of MY solution which are combined are selected in such a manner that the FDCA concentration in the reaction mixture is within the range of 1-10 wt. %, in some embodiments 2 to 8 wt. % calculated on the total weight of the reaction mixture.

6. Method according to claim 1, wherein at least 50 vol. % of the MY solution resulting from the solid/liquid separation step is provided to the step of combining MFDC with HY.

7. Method according to claim 1, wherein the concentration of the MY solution, e.g., the magnesium chloride solution, withdrawn from the solid liquid separation step has a concentration of at least 5 wt. %, and/or at most 30 wt. %.

8. Method according to claim 1, wherein the MFDC results from a fermentation step.

9. Method according to claim 1, wherein of the HY solution resulting from the solid/liquid separation step, a part is recycled to the combination step, and another part is not recycled to the combination step.

10. Method according to claim 9, wherein the HY solution is a magnesium chloride solution, and part of the magnesium chloride stream which is not recycled to the combination step is subjected to a thermal decomposition step, wherein magnesium chloride is reacted with water to form hydrochloric acid and magnesium oxide.

11. Method according to claim 10, wherein hydrochloric acid resulting from the thermal decomposition is provided to the combination step, in gaseous form, or after having been incorporated in an aqueous solution.

12. Method according to claim 10, wherein the magnesium oxide is provided, directly or after conversion into magnesium hydroxide or magnesium carbonate, as neutralizing agent to a fermentation process.

\* \* \* \* \*